United States Patent [19]
Powell

[11] 4,155,979
[45] May 22, 1979

[54] COMBINATION INCENSE BURNER AND INCENSE STORAGE DEVICE

[76] Inventor: Joseph Powell, 563 Montgomery St., Apt. 97-2, Jersey City, N.J. 07302

[21] Appl. No.: 932,478

[22] Filed: Aug. 10, 1978

[51] Int. Cl.² ............................................. A61L 9/02
[52] U.S. Cl. .................................. 422/126; 422/239; 422/306; 431/296
[58] Field of Search ................ 422/126, 5, 239, 306; 431/296

[56] References Cited

U.S. PATENT DOCUMENTS

| | | | |
|---|---|---|---|
| 721,133 | 2/1903 | Ahne | 422/126 |
| 1,450,790 | 4/1923 | Bentley | 422/126 |
| 1,609,814 | 12/1926 | Gray et al. | 422/126 |
| 1,613,777 | 1/1927 | Wom | 422/126 |
| 2,038,814 | 4/1936 | Van Riper | D48/2 X |
| 2,131,460 | 9/1938 | White | 422/126 |
| 2,681,827 | 6/1954 | Racz | 422/123 X |
| 2,757,278 | 7/1956 | Cloud | 422/5 X |
| 2,818,615 | 1/1958 | Burness | 422/5 |

OTHER PUBLICATIONS

"Ashcatcher" advertisement, (Hobbit Pipes); *High Times;* Dec. 1976.

*Primary Examiner*—Barry S. Richman
*Attorney, Agent, or Firm*—Gloria K. Koenig

[57] ABSTRACT

A device having an upright backplate formed with a pocket for holding sticks of incense and means to suspend the back plate from a door, a horizontally positioned elongated base member formed with a longitudinal channel and with a separate recess for supporting a romovable chimney which is provided with a cap having spaced openings. means are provided to hold a stick of incense in a horizontal position over the longitudinal channel to burn incense in the open and to provide a place in which ashes may fall. Means are also provided in the recess to hold the stick of incense in an upright position to burn within the chimney, the smoke escaping through the holes in the cap and the ashes collecting in the recess. The back plate and base member are separable to permit the base member to be used separately and for ease of storage of the device.

2 Claims, 5 Drawing Figures

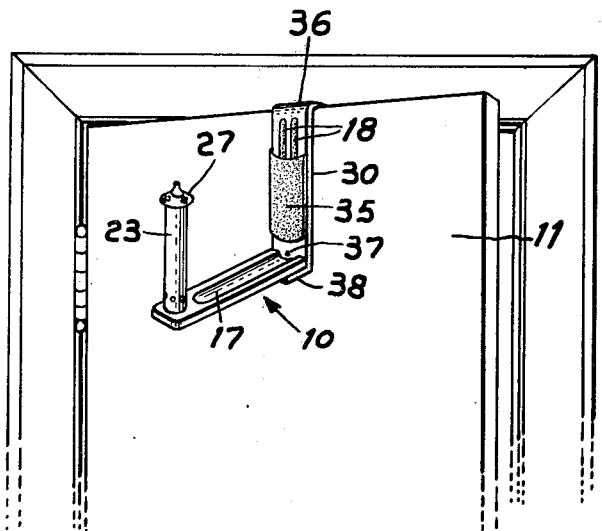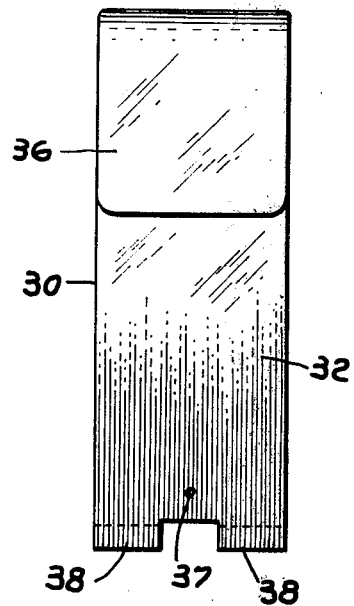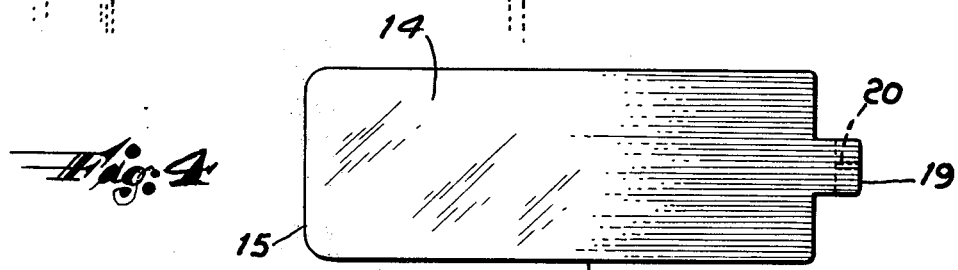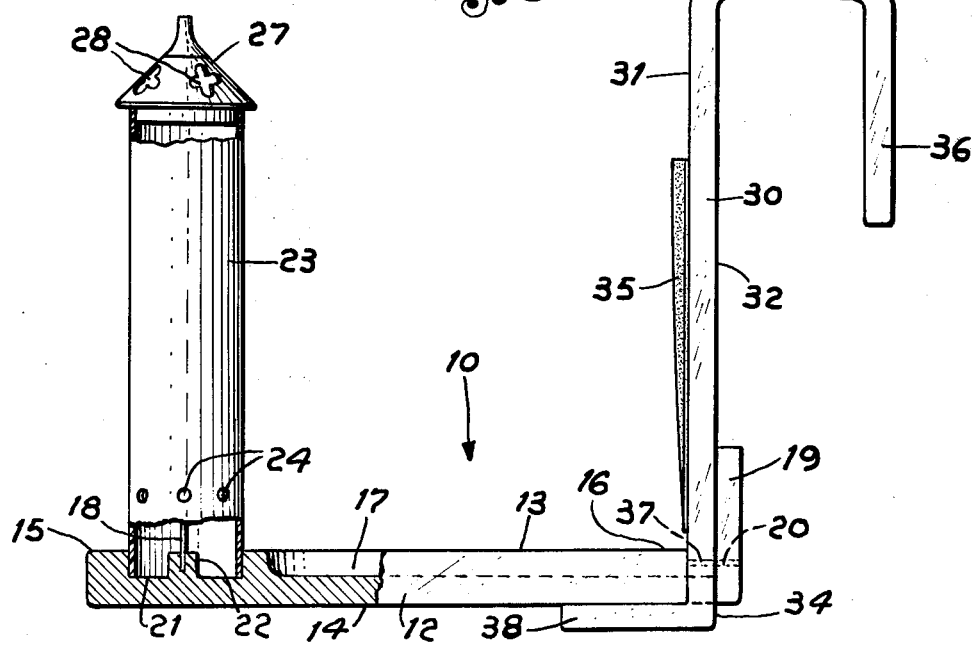

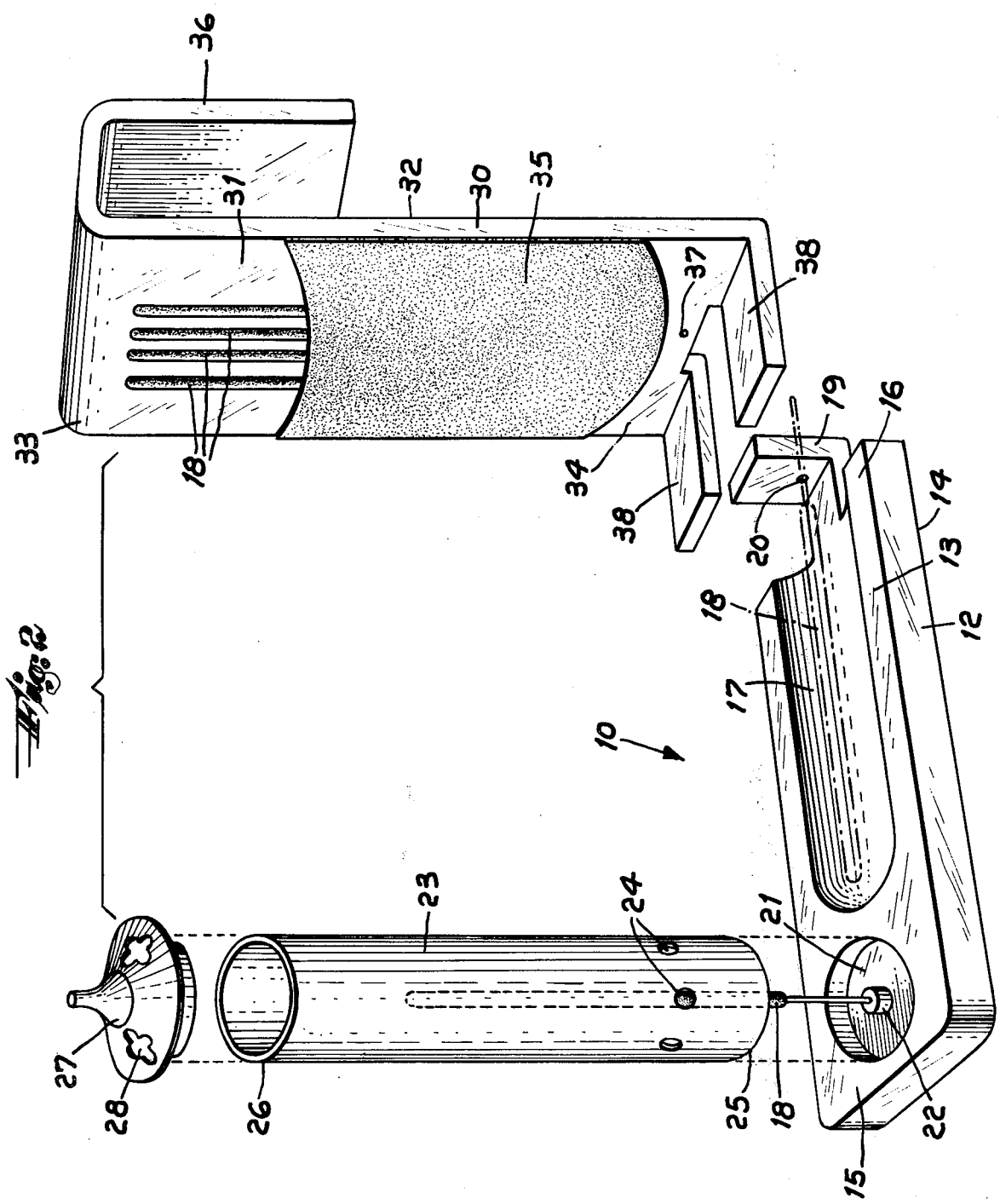

COMBINATION INCENSE BURNER AND INCENSE STORAGE DEVICE

BACKGROUND OF THE INVENTION (1) Field of the Invention

This invention relates to a combination incense burner and incense storage device which permits the parts to be detached for use separately and for storage purposes.

(2) Description of the Prior Art

Prior inventions in the field of incense burners have provided means to either burn incense in the open by mounting in a holder or have provided a chimney device of complex design which would be expensive to manufacture. None of the prior inventions known to the inventor have provided a combination storage device and incense burner which allow for two separate methods of burning incense.

SUMMARY OF THE INVENTION

This invention is a combination incense burner and incense storage device the parts of which may be detached for use separately and for ease in storing the device. When fully assembled, the device is hung over a door with its base member extending perpendicularly from the door. A pocket formed on the back plate holds sticks of incense. The incense stick may be burned in a horizontal position open to the air with the ash dropping into a longitudinal depression formed in the base member or the stick of incense may be mounted in an upright position inside of a chimney which extends upwardly from a separate recess formed in the front end of the base member. When fully assembled and hung onto a door the device is neat and compact. The chimney serves as a safety enclosure for burning incense by preventing accidental burns and flying sparks. Burning incense within the chimney reduces eye irritation by directing the smoke in an upward direction in the room. When the parts are separated, the back plate may be left suspended on the door as a convenient storage place for incense sticks. The base member may then be placed on a flat surface, such as a table, and used to burn incense in an open position with the chimney removed or within the chimney as described above. When not used for burning incense, the chimney may be removed and the base member may be used as an ordinary ash tray.

It is an object of this invention to provide a device which provides a means to store incense sticks conveniently as well as to burn incense in a variety of ways.

It is a further object of this invention to provide a device which is small and inexpensive to manufacture.

These and various other objects and advantages of this invention will be more fully apparent from a consideration of the following description, drawings and appended claims.

BRIEF DESCRIPTION OF THE DRAWINGS

FIG. 1 is a perspective view of the device mounted on a door.

FIG. 2 is an exploded view of the device, the parts being shown in perspective.

FIG. 3 is a partly sectional view of the device.

FIG. 4 is a bottom plan view of the base member.

FIG. 5 is a plan view of the back of the back plate.

DESCRIPTION OF THE PREFERRED EMBODIMENTS

Referring now specifically to the drawings, the numeral 10 designates the combination incense burner and storage device shown in FIG. 1 mounted on the top a door 11. A base member 12 is formed with a top face 13, a flat bottom face 14, a front end 15 and a back end 16. A longitudinal channel 17 of predetermined length is formed in the top face 13 of the base member 12 extending from the back end toward the front end 15 of the base member, terminating a predetermined distance from the front end 15. The length of the longitudinal channel 17 is sufficient to extend beyond the length of a stick of incense mounted horizontally over the channel. Means to hold a stick of incense over the longitudinal channel 17 are provided by an extension or tongue 19 projecting upwardly from the back end 16 of the base member in alignment with the longitudinal channel 17, the tongue being formed with an opening 20 to hold the end of the incense stick 20. When mounted in the opening 20, an incense stick will be held over the channel and may be burned completely with the ash being caught in the longitudinal channel.

A separate recess 21 is formed in the top face 13 of the base member 12 forward of the longitudinal channel 17. Means to hold a stick of incense are provided in the center of the recess. As shown in the drawings, a cup 22 is formed in the center of the recess 21 to hold a stick of incense in an upright position vertical to the base member 12. Alternatively, a piece of porous, spongy material which can be easily perforated can be affixed to the center of the recess to hold the incense stick in an upright position. A removably mounted chimney member 23 extends upwardly from the recess 21, the chimney member being provided with spaced openings 24 around its lower end 25 to provide an upward draft of air to the burning incense. The chimney member 23 is of a predetermined height to extend above the top of a stick of incense mounted in the recess 21. A cap 27 formed with spaced openings 28 is removably mounted on the upper end 26 of the chimney. When the incense is burning within the chimney 23 with the cap 27 mounted thereon, the upward draft of air through the spaced openings 24 at the lower end of the chimney forces the incense smoke out through the spaced openings 28 in the cap.

A back plate 30 is formed to be removably mounted onto the back end 16 of the base member 12 and to extend upward from and perpendicular to the base member 12. The back plate 30 has a front face 31, back face 32, upper end 33 and lower end 34. A pocket 35 is formed on the front face 31 to hold sticks of incense. Downwardly opening and backward extending hooking means 36 are formed at the upper end 33 of the back plate 30 to provide a means to mount the back plate over the upper edge of a door 11. As shown in the drawings, the entire upper end of the back plate is bent backward to form a single hook, but a plurality of individual hooks could be attached to the upper end of the back plate to provide a means for mounting the back plate on a door. A small opening 37 is formed in the lower end 34 of the back plate 30 in alignment with the opening 20 of the upward extending tongue 19 of the base member 12, thereby providing a small channel in which to support a stick of incense in a horizontal position.

The back plate 30 may be removably mounted to the base member by a variety of commercially available hinge devices. As shown in the drawings, two rigid extensions or tongues 38 project outwardly from the lower end 34 of the back plate 30. The extensions 38 are spaced to permit the back plate 30 to be interlocked with the base member 12 by having the upward extending tongue 19 of the base member 12 pass between the extensions 38 of the back plate and press against the backface of the back plate, while the extensions of the back plate slide under the back end 16 of the base member 12 to support it and hold it horizontally by the downward pressure of the base member 12 itself. When the back plate 30 and base member 12 are attached, and the device hung on a door, incense may be burned in an elevated position in a room. Alternatively, the base member may be set on a table for use while the back plate 30 remains hooked on the door to provide a convenient storage place for sticks of incense. It will thus be seen that I have provided a new and improved combination incense burner and storage device.

I claim:

1. A combination incense burner and incense storage device comprising:
    (a) a base member having a top face, a flat bottom face, a front end and a back end, the top face being formed with
        (1) a longitudinal channel of predetermined length extending from the back end toward the front end of the base member and terminating a predetermined distance from the front end, and
        (2) a separate recess forward of the longitudinal channel;
    (b) means for holding a stick of incense in an upright position vertical to the base member in the center portion of the recess;
    (c) a chimney removably mounted in the recess and extending upwardly therefrom, the chimney being provided with spaced openings around its lower end, the chimney being of a predetermined height to extend above the top of a stick of incense mounted in the recess;
    (d) a removable cap fitting the upper end of the chimney, the cap having spaced openings;
    (e) a tongue projecting upwardly from the back end of the base member in alignment with the longitudinal channel, the tongue being formed with an opening to hold the end of an incense stick over the longitudinal channel;
    (f) a back plate having a front face, back face, upper end and lower end and formed with a small opening in the lower end;
    (g) means to removably mount the back plate to the base member, the back plate being removably mounted onto the back end of the base member to extend upward from and perpendicular to the base member, the opening in the lower end of the back plate being in alignment with the opening in the tongue of the base member;
    (h) a storage pocket formed on the front face of the back plate; and
    (i) downwardly opening hook means extending back from the upper end of said back plate, the back plate thereby being adapted for attaching the device over the top of a door.

2. A combination incense burner and storage device as set out in claim 1 wherein the means for holding a stick of incense in the recess comprises a cup formed in the center of the recess.

* * * * *